United States Patent [19]
Boudjouk et al.

[11] Patent Number: 5,942,637
[45] Date of Patent: Aug. 24, 1999

[54] COMPOUNDS CONTAINING TETRADECACHLOROCYCLOHEXASILANE DIANION

[75] Inventors: Philip Raymond Boudjouk; Beon-Kyu Kim; Michael Perry Remington; Bhanu Chauhan, all of Fargo, N. Dak.

[73] Assignee: North Dakota State University Research Foundation, Fargo, N. Dak.

[21] Appl. No.: 09/050,141

[22] Filed: Mar. 30, 1998

[51] Int. Cl.$^6$ ................................. C07F 7/08; C07F 7/10
[52] U.S. Cl. ................. 556/424; 568/9; 568/17; 423/341; 423/342
[58] Field of Search ................. 556/424; 568/9, 568/17; 423/341, 342

[56] References Cited

U.S. PATENT DOCUMENTS 4,841,083  6/1989  Nagai et al. ........................ 423/341 X

OTHER PUBLICATIONS

Kaczmarczyk et al. Journal of American Chemical Society, vol. 82, p. 751, 1960.
Kaczmarczyk et al. Journal of Inorganic Nuclear Chemistry, vol. 17, pp. 186–188, 1961.
Wiber et al. Angew. Chem. Int. Ed., vol. 1, No. 9, p. 517, 1962.
Hengge et al. Angew. Chem. Int. Ed., vol. 16, No. 6, p. 403, 1977.

*Primary Examiner*—Paul F. Shaver
*Attorney, Agent, or Firm*—James E. Bittell; Larry A. Milco

[57] ABSTRACT

Compounds containing a tetradecachlorocyclohexasilane dianion are prepared by contacting trichlorosilane with a reagent composition comprising a tertiary polyamine. The compound [pedeta.SiH$_2$Cl$^{+1}$]$_2$[Si$_6$Cl$_{14}^{-2}$] wherein pedeta is N,N,N',N'',N''-pentaethyldiethylenetriamine is prepared by contacting trichlorosilane with pedeta. The compound [Ph$_4$P$^{+1}$]$_2$[Si$_6$Cl$_{14}^{-2}$] is prepared by contacting trichlorosilane with a mixture of N,N,N',N'-tetraethylethylenediamine and triphenylphosphonium chloride. The tetradecachlorocyclohexasilane dianion can be chemically reduced to cyclohexasilane, a compound useful in the deposition of amorphous silicon films. The tetradecachlorcyclohexasilane dianion can also be contacted with a Grignard reagent to form a dodecaorganocyclohexasilane.

23 Claims, 2 Drawing Sheets

TOP VIEW

*= AVERAGE VALUE

1

COMPOUNDS CONTAINING TETRADECACHLOROCYCLOHEXASILANE DIANION

FIELD OF THE INVENTION

The present invention relates to compounds containing a tetradecachlorocyclohexasilane dianion and to the preparation of such compounds by an amine-promoted coupling reaction of trichlorosilane. This invention also relates to methods of preparing cyclohexasilane and dodecaorganocyclohexasilanes.

BACKGROUND OF THE INVENTION

It is well known in the art that the Wurtz-type coupling of haloorganosilanes provides a useful synthetic route to polysilanes. For example, linear polysilanes can be prepared by the alkali-metal reductive coupling of dichloroorganosilanes and branched polysilanes can be prepared by the reductive coupling of trichloroorganosilanes.

However, only a limited number of amine-promoted coupling reactions of silanes are known in the art. These reactions are not generally useful for the preparation of polysilanes. For example, Kaczmarczyk et al. disclose the disproportionation of disilicon hexachloride in the presence of trimethylamine to yield either hexasilicon tetradecachloride (J. Amer. Chem. Soc. 82, 751, 1960) or pentasilicon dodecachloride (J. In org. Nucl. Chem. 17, 186–188, 1961), depending on the reaction conditions. Wiber et al. teach the synthesis of pentasilicon dodecachloride by treatment of disilicon hexachloride with trimethylamine using a modification of the reaction conditions described by Kaczmaryk et al. for the preparation of hexasilicon tetradecachloride (Angew. Chem. Int. Ed., 1, No. 9, 517, 1962).

The present inventors have discovered an amine-promoted coupling reaction of trichlorosilane that produces novel compounds containing a tetradecachlorocyclohexasilane dianion.

SUMMARY OF THE INVENTION

The present invention is directed to a compound containing a tetradecachlorocyclohexasilane dianion.

This invention is also directed to a method of preparing a compound containing a tetradecachlorocyclohexasilane dianion, said method comprising the steps of:

A) contacting trichlorosilane with a reagent composition comprising a tertiary polyamine; and (B) recovering a compound containing a tetradecachlorocyclohexasilane dianion.

The present invention is further directed to a method of preparing cyclohexasilane, said method comprising contacting a compound containing a tetradecachlorocyclohexasilane dianion with a metal hydride reducing agent.

The present method produces cyclohexasilane, a compound useful in the deposition of amorphous silicon films, in fewer steps compared to the conventional method reported by Hengge et al (Angew. Chem. Int. Ed. 16, No. 6, 403, 1977). Moreover, the present method of preparing cyclohexasilane obviates the difficulties associated with isolating the dodecaphenylcyclohexasilane intermediate in the prior art synthesis.

This invention is still further directed to a method of preparing a dodecaorganocyclohexasilane, said method comprising contacting a compound containing a tetradecachlorocyclohexasilane dianion with a reagent having the formula RMgX wherein R is alkyl or aryl and X is chloro, bromo, or iodo.

These and other features, aspects, and advantages of the present invention will become better understood with regard to the following drawing, description, and appended claims.

DETAILED DESCRIPTION OF THE INVENTION

Figure 1:
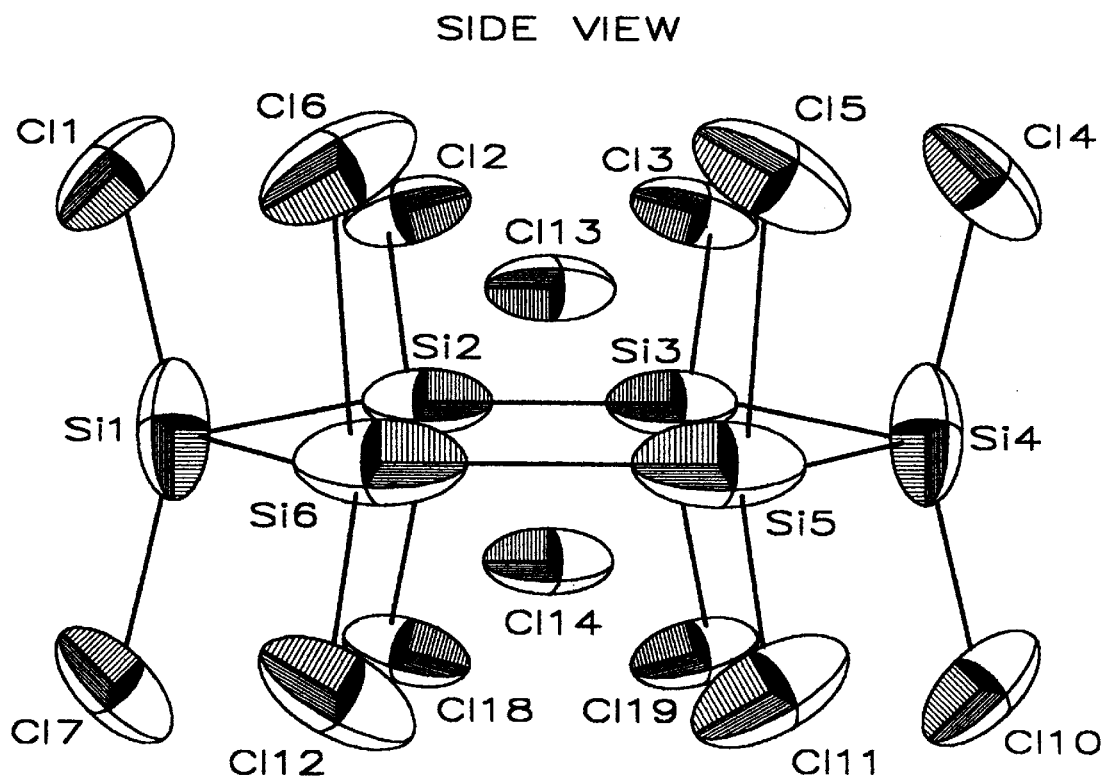
FIG. 1 shows the molecular structure of the tetradecachlorocyclohexasilane dianion, $Si_6Cl_{14}^{-2}$, as determined by X-ray diffraction.
Figure 2:
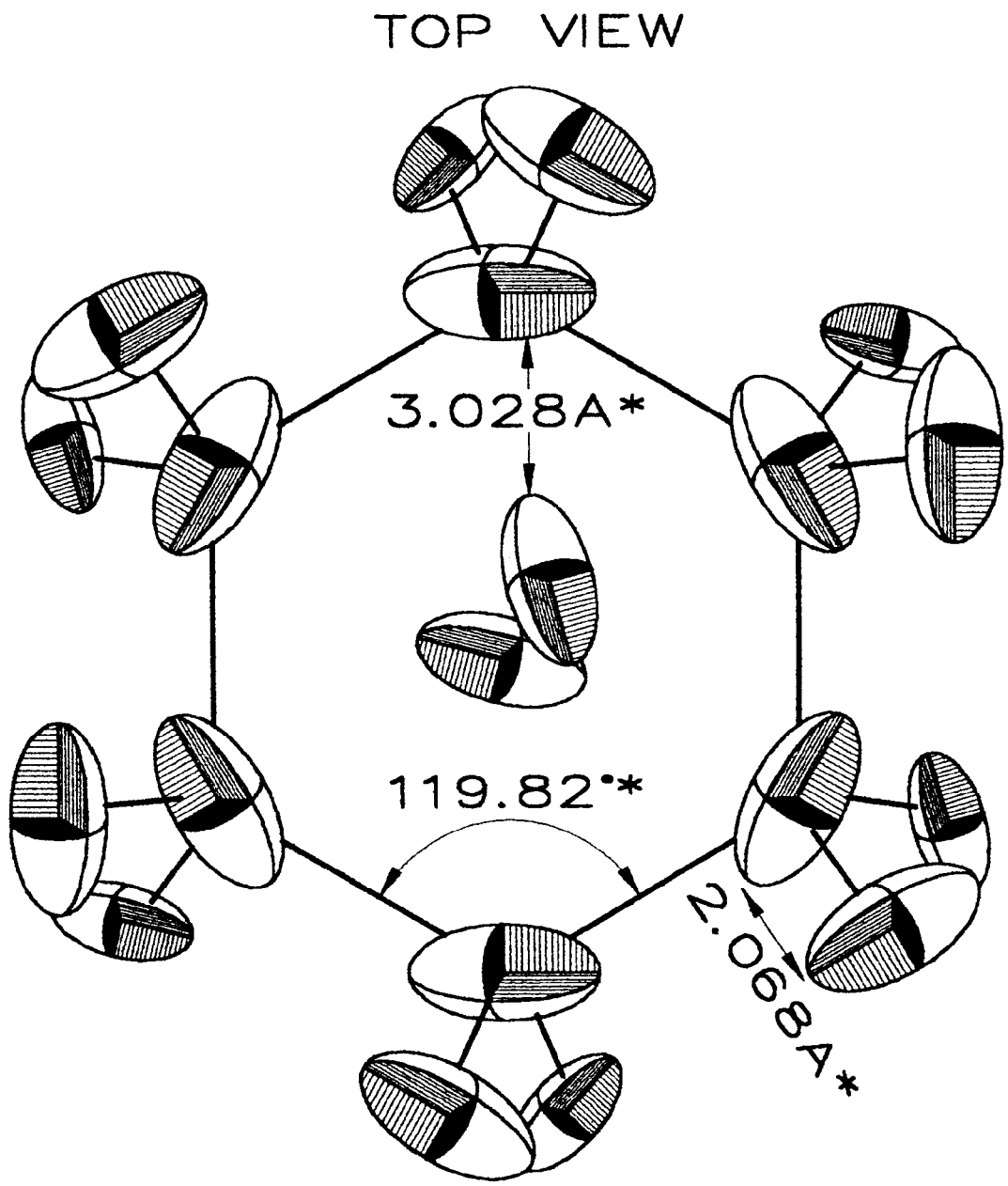
FIG. 2 shows the top view of the anion.

In the present application, the term "pedeta" represents N,N,N',N",N"-pentaethyldiethylenetriamine and the term "teeda" denotes N,N,N',N'-tetraethylethylenediamine.

The compounds of the present invention contain a tetradecachlorocyclohexasilane dianion. The counterion in the compounds can be any cation that forms a stable salt with the tetradecachlorocyclohexasilane dianion. Preferably the compound containing the tetradecachlorocyclohexasilane dianion has the formula $[X^{+1}]_2[Si_6Cl_{14}^{-2}]$ wherein X is pedeta·$SiH_2Cl$ or $Ph_4P$ and wherein pedeta is N,N,N',N",N"-pentaethyldiethylenetriamine.

The compounds of the present invention are prepared by contacting trichlorosilane with a reagent composition comprising a tertiary polyamine and recovering the compound containing the tetradecachlorocyclohexasilane dianion. The tertiary polyamine contains at least two tertiary nitrogen atoms and preferably contains two or three tertiary nitrogen atoms. Suitable tertiary polyamines include nitrogen-substituted derivatives of ethylenediamine and diethylenetriamine wherein the substituents are alkyl having 1 to 4 carbon atoms or aryl.

In a preferred embodiment of this invention, trichlorosilane is contacted with N,N,N',N",N"-pentaethyldiethylenetriamine and the compound having the formula $[pedeta·SiH_2Cl^{+1}]_2[Si_6Cl_{14}^{-2}]$ is recovered from the mixture. In another preferred embodiment, trichlorosilane is contacted with a mixture of N,N,N',N'-tetraethylethylenediamine and triphenylphosphonium chloride and the compound having the formula $[Ph_4P^{+1}]_2[Si_6Cl_{14}^{-2}]$ is recovered from the mixture.

The trichlorosilane can be contacted with the reagent composition in any standard reactor suitable for contacting a chlorosilane with another reactant. The reactor can be, for example, a continuous-stirred batch type reactor, semi-batch type reactor, or a continuous type reactor.

The present method is preferably carried out under substantially anhydrous conditions. This can be accomplished by purging the reactor with a dry inert gas such as nitrogen or argon and thereafter maintaining a blanket of such gas in the reactor.

Although the compound containing the tetradecachlorocyclohexasilane dianion can be prepared in the absence of a diluent, the step of contacting trichlorosilane with the reagent composition is preferably carried out in the presence of an organic solvent. Any organic solvent or mixture of organic solvents that does not interfere with the coupling reaction of trichlorosilane to form the tetradecachlorocyclohexasilane dianion can be used. Preferably, the organic solvent is a chlorinated hydrocarbon such as chloroform, dichloromethane, and 1,2-dichloroethane. More preferably, the organic solvent is dichloromethane. When present, the volume of the organic solvent is typically from 0.01 to 100 and preferably 1 to 10 times the combined volume of trichlorosilane and the reagent composition.

The trichlorosilane can be contacted with the reagent composition at a temperature of from 0° C. to 120° C. Higher temperatures may be achieved under elevated pressures or in a higher boiling solvent under reflux conditions. Preferably, trichlorosilane is contacted with the reagent composition at a temperature of from 15° C. to 30° C.

The mole ratio of trichlorosilane to the reagent composition can vary over a wide range. In the preparation of the preferred compound [pedeta·$SiH_2Cl^{+1}$]$_2$[$Si_6Cl_{14}{}^{-2}$], the mole ratio of trichlorosilane to pedeta is typically from 0.1:1 to 10:1 and preferably from 2:1 to 4:1. In the preparation of the preferred compound [$Ph_4P^{+1}$]$_2$[$Si_6Cl_{14}{}^{-2}$], the mole ratio of trichlorosilane to teeda to $Ph_4PCl$ is typically from 20:20:1 to 1:1:1 and preferably from 10:7:1 to 2:2:1.

Preferably, the compound containing the tetradecachlorocyclohexasilane dianion is recovered from the reaction mixture by crystallization or precipitation. For example, recovery of the compound containing the tetradecachlorocyclohexasilane dianion can be achieved by adding sufficient quantity of an organic solvent that effects crystallization of the compound. Crystallization may take place at room temperature or below, for example, −20° C. Alternatively, the compound containing the tetradecachlorcyclohexasilane dianion can be recovered from the reaction mixture by adding sufficient quantity of an organic solvent that effects precipitation of the compound.

Any organic solvent or mixture of such solvents that effects crystallization or precipitation of the compound containing the tetradecachlorocyclohexasilane dianion from the reaction mixture and does not react with the compound being recovered may be used in the present method. Examples of suitable organic solvents include hydrocarbons such as pentane, hexane, and heptane, octane, and nonane; and ethers such as diethyl ether and tetrahydrofuran. Preferably, the organic solvent used for effecting crystallization or precipitation of the compounds of the present invention is pentane, hexane, or heptane, octane, or nonane. More preferably, the organic solvent is pentane.

The tetradecachlorocyclohexasilane dianion can be chemically reduced to cyclohexasilane. The reduction reaction can be carried out by contacting the compound containing the tetradecachlorocyclohexasilane dianion with a metal hydride reducing agent in an organic solvent at a temperature of from −110° C. to 150° C. Preferably the compound containing the tetradecachlorocyclohexasilane dianion has the formula [$X^{+1}$]$_2$[$Si_6Cl_{14}{}^{-2}$] wherein X is defined above. Also, preferably, the reducing agent is lithium aluminum hydride or diisobutylaluminum hydride.

The tetradecachlorocyclohexasilane dianion can also be contacted with a Grignard reagent to form a dodecaorganocyclohexasilane. The Grignard reagent is represented by the formula RMgX wherein R is alkyl or aryl and X is chloro, bromo, or iodo. Suitable R groups include, but are not limited to, methyl, ethyl, propyl, t-butyl, and phenyl. Preferably the compound containing the tetradecachlorocyclohexasilane dianion has the formula [$X^{+1}$]$_2$[$Si_6Cl_{14}{}^{-2}$] wherein X is defined above. The reaction of the compound containing the tetradecachlorocyclohexasilane dianion with Grignard reagents can be performed by standard methods known in the art for reacting chlorosilanes with Grignard reagents.

The following examples are presented to further illustrate the compositions of this invention, but are not to be considered as limiting the invention, which is delineated in the appended claims.

EXAMPLES

All reactions were performed in a glass flask under a blanket of dry nitrogen. Trichlorosilane was distilled before use. N,N,N',N'',N''-pentaethyldiethylenetriamine (pedeta) was distilled from sodium metal under a nitrogen atmosphere. N,N,N',N' tetraethylethylenediamine (teeda) was refluxed over $CaH_2$ and then distilled under a nitrogen atmosphere. Dichloromethane was distilled from $P_2O_5$ under a nitrogen atmosphere just prior to use. Materials were added to the flask through a rubber septum by means of a syringe.

Example 1

This example demonstrates the preparation of [pedeta·$SiH_2Cl^{+1}$]$_2$[$Si_6Cl_{14}{}^{2-}$]. Trichlorosilane (5.52 g; 41.0 mmol) was added to a clear, colorless solution of N,N,N',N'',N''-pentaethyldiethylenetriamine (4.0 g, 16 mmol) in dichloromethane (50 mL) under an atmosphere of dry nitrogen gas. A slight warming of the reaction vessel contents occurred upon addition. After stirring for 24 h at room temperature, dry, olefin-free hexane (10 mL) was added to the reaction mixture. The mixture was allowed to stand for 3 days at room temperature, during which time white crystals slowly deposited from solution. The crystals (1.8 g, 1.4 mmol) were isolated by filtration under nitrogen. The reaction proceeded with greater than 95% conversion of the starting materials, as determined by $^1$HNMR. IR (KBr) 2202 cm$^{-1}$; mp 102–103° C.; elemental analysis calculated for [pedeta·$SiH_2Cl^{+1}$]$_2$ [$Si_6Cl_{14}{}^{2-}$]: C, 26.22; H, 5.50; N, 6.55. Found C, 26.20; H, 5.47; N, 6.49.

Elemental analysis, infrared spectroscopy and X-ray analysis confirmed that these crystals are a salt having the formula [pedeta·$SiH_2Cl^{+1}$]$_2$[$Si_6Cl_{14}{}^{-2}$]. The salt is composed of 2 identical cationic parts in which the silicon atom is hexacoordinated to three nitrogen atoms from pedeta, 2 hydrogen atoms and one chlorine atom. The two hydrogen atoms occupy the axial positions and the four equatorial positions are occupied by the three nitrogen atoms and the chlorine atom. In the dianion part of the salt, the six silicon atoms form a planar six-membered ring. The 14 chlorine atoms are of two kinds: a set of twelve equivalent chlorine atoms bonded in pairs to each of the six silicon atoms and a set of two chlorine atoms located on the six fold axis of the ring. The structure of $Si_6Cl_{14}{}^{2-}$ is illustrated in FIG. 1.

Example 2

This example demonstrates the preparation of [$Ph_4P^{+1}$]$_2$ [$Si_6Cl_{14}{}^{2-}$]. Trichlorosilane (5.4 g; 39 mmol) was added to a clear, colorless solution of N,N,N',N'-tetraethylethylenediamine (3.4 g, 20 mmol) and tetraphenylphosphonium chloride (5.0 g, 13 mmol) in dichloromethane (50 mL) under an atmosphere of dry nitrogen gas. A slight warming of the reaction vessel contents occurred upon addition. After stirring for 24 h at room temperature, dry, olefin-free hexane (10 mL) was added to the reaction mixture. The mixture was allowed to stand for 3 days at room temperature, during which time white crystals slowly deposited from solution. The crystals (0.7 g, 0.52 mmol) were isolated by filtration under nitrogen. The reaction proceeded with greater than 95% conversion of the starting materials, as determined by $^1$HNMR. Elemental analysis, infrared spectroscopy and X-ray analysis confirmed that these crystals are a salt having the formula [$Ph_4P^+$]$_2$ [$Si_6Cl_{14}{}^{-2}$]. IR (KBr) 3110, 1100, 540 cm$^{-1}$; mp (decomposition) 250° C.; elemental analysis calculated for [$Ph_4P^{+1}$]$_2$ [$Si_6Cl_{14}{}^{2-}$]: C, 42.91; H, 3.00. Found C, 43.89; H, 3.20.

Example 3

This example demonstrates the preparation of cyclohexasilane from [pedeta·$SiH_2Cl^{+1}$]$_2$[$Si_6Cl_{14}{}^{-2}$] and lithium aluminum hydride. A mixture of [pedeta·$SiH_2Cl^{+1}$]$_2$[$Si_6Cl_{14}{}^{-2}$]

(7.31 g, 5.74 mmol) and lithium aluminum hydride (1.08 g, 28.5 mmol) was placed in dry, nitrogen filled, round bottom flask containing a magnetic stir bar. Dry diethyl ether (115 mL) was added and the resulting slurry was stirred for 3 h at which time the reaction was complete as determined by $^1$HNMR spectroscopy. During the course of the reaction SiH$_4$ was produced as a gas and trapped in a degassed aqueous solution of potassium hydroxide. The solution was decanted from the salts, cooled, and filtered to remove remaining salts. These operations were carried out under an inert gas atmosphere. Analysis of the solution by $^1$HNMR spectroscopy indicated that cyclohexasilane was formed as the dominant silicon-containing product in an estimated yield of greater than 80%. $^1$H NMR (270 MHz, C$_6$D$_6$) δ 3.35, $^{29}$Si NMR (C$_6$D$_6$) δ–106.96; J$_{Si-H}$=195 Hz.

Example 4

This example demonstrates the preparation of cyclohexasilane from [pedeta·SiH$_2$Cl$^{+1}$]$_2$[Si$_6$Cl$_{14}$$^{-2}$] and diisobutylaluminum hydride. A solution of [pedeta·SiH$_2$Cl$^{+1}$]$_2$[Si$_6$Cl$_{14}$$^{-2}$] (0.57 g; 0.44 mmol) and benzene (20 mL) was placed in dry, nitrogen filled, round bottom flask containing a magnetic stir bar. Diisobutylaluminum hydride in hexane (7.12 mL of a 1.0M solution, 7.12 mmol) was added. Cyclohexasilane was formed in greater than 90% yield as determined by $^1$HNMR spectroscopy. $^1$H NMR (270 MHz, C$_6$D$_6$) δ 3.33; $^{29}$Si NMR (C$_6$D$_6$) δ–107.55; J$_{Si-H}$=200 Hz.

Example 5

This example demonstrates the preparation of dodecamethylcyclohexasilane from [pedeta·SiH$_2$Cl]$_2$[Si$_6$Cl$_{14}$$^{-2}$]. Tetrahydrofuran (15 mL) and [pedeta·SiH$_2$Cl$^{+1}$]$_2$[Si$_6$Cl$_{14}$$^{-2}$] (1.0 g, 0.78 mmol) were combined in a dry, three-neck flask under nitrogen. To this mixture was added methylmagnesium bromide (12.4 mmol). After stirring for 24 h at room temperature, the reaction mixture was hydrolyzed and extracted with hexane and ether. The combined extracts were concentrated under reduced pressure. Evacuation of the residue under high vacuum overnight gave dodecamethylcyclohexasilane (0.23 g, 0.66 mmol, 85% yield). $^1$H NMR (270 MHz, C$_6$D$_6$) δ 0.22; $^{13}$CNMR (C$_6$D$_6$) δ–6.15; $^{29}$SiNMR (C$_6$D$_6$) δ–41.73.

That which is claimed is:

1. A compound containing a tetradecachlorcyclohexasilane dianion.

2. The compound according to claim 1, having the formula [X$^{+1}$]$_2$[Si$_6$Cl$_{14}$$^{-2}$] wherein X is pedeta.SiH$_2$Cl or Ph$_4$P and wherein pedeta is N,N,N',N",N"-pentaethyldiethylenetriamine.

3. A method of preparing a compound containing a tetradecachlorocyclohexasilane dianion, said method comprising the steps of:

(A) contacting trichlorosilane with a reagent composition comprising a tertiary polyamine; and
   (B) recovering compound containing a tetradecachlorocyclohexasilane dianion.

4. The method according to claim 3, wherein said step of contacting trichlorosilane with the reagent composition is carried out in the presence of an organic solvent.

5. The method according to claim 4, wherein the organic solvent is selected from the group consisting of chloroform, dichloromethane, and 1,2-dichlorethane.

6. The method to claim 5, wherein the organic solvent is dichloromethane.

7. The method according to claim 4, wherein the organic solvent has a volume of from 1 to 10 times the combined volume of trichlorosilane and the reagent composition.

8. The method according to claim 4, wherein said step of contacting trichlorosilane with the reagent composition is carried out at a temperature of from 15° C. to 30° C.

9. The method according to claim 4, wherein said step of recovering the compound containing the tetradecachlorocyclohexasilane dianion is achieved by adding an organic solvent that effects crystallization of the compound.

10. The method according to claim 9, wherein the organic solvent that effects crystallization of the compound is pentane, hexane, heptane, octane, or nonane.

11. The method according to claim 4, wherein said step of recovering the compound containing the tetradecachlorocyclohexasilane dianion is achieved by adding an organic solvent that effects precipitation of the compound.

12. The method according to claim 11, wherein the organic solvent that effects precipitation of the compound is pentane, hexane, heptane, octane, or nonane.

13. The method according to claim 3, wherein the reagent composition comprises N,N,N',N",N"-pentaethyldiethylenetriamine and the compound containing the tetradecachlorcyclohexasilane dianion has the formula [pedeta.SiH$_2$Cl$^{+1}$]$_2$[Si$_6$Cl$_{14}$$^{-2}$] wherein pedeta is N,N,N',N", N"-pentaethyldiethylenetriamine.

14. The method according to claim 13, wherein said step of contacting trichlorosilane with the reagent composition is carried out in the presence of an organic solvent.

15. The method according to claim 14, wherein the mole ratio of trichlorosilane to N,N,N',N",N"-pentaethyldiethylenetriamine is from 2:1 to 4:1.

16. The method according to claim to claim 3, wherein the reagent composition comprises a mixture of N,N,N',N'-tetraethylethylenediamine and tetraphenylphosphonium chloride and the compound containing the tetradecachlorocyclohexasilane dianion has the formula [Ph$_4$P$^{+1}$]$_2$[Si$_6$Cl$_{14}$$^{-2}$].

17. The method according to claim 16, wherein said step of contacting trichlorosilane with the reagent composition is carried out in the presence of an organic solvent.

18. The method according to claim 17, wherein the mole ratio of trichlorosilane to N,N,N',N'-tetraethylethylenediamine to tetraphenylphosphonium chloride is from 10:7:1 to 2:2:1.

19. A method of preparing cyclohexasilane, said method comprising contacting a compound containing a tetradecachlorocyclohexasilane dianion with a metal hydride reducing agent.

20. The method according to claim 19, wherein the compound containing the tetradecachlorocyclohexsilane dianion has the formula [X$^{+1}$]$_2$[Si$_6$Cl$_{14}$$^{-2}$] wherein X is pedeta.SiH$_2$Cl or Ph$_4$P and wherein pedeta is N,N,N',N", N"-pentaethyldiethylenetriamine.

21. The method according to claim 19, wherein the metal hydride reducing agent is lithium aluminum hydride or diisobutylaluminum hydride.

22. A method of preparing a dodecaorganocyclohexasilane, said method comprising contacting a compound containing a tetradecachlorocyclohexasilane dianion with a reagent having the formula RMgX wherein R is alkyl or aryl and X is chloro, bromo, or iodo.

23. The method according to claim 22, wherein the compound containing the tetradecachlorocyclohexasilane dianion has the formula [X$^{+1}$]$_2$[Si$_6$Cl$_{14}$$^{-2}$] wherein X is pedeta.SiH$_2$Cl or Ph$_4$P and wherein pedeta is N,N,N',N", N"-pentaethyldiethylenetriamine.

\* \* \* \* \*